United States Patent [19]

Guay et al.

[11] Patent Number: 5,192,532

[45] Date of Patent: *Mar. 9, 1993

[54] ORAL COMPOSITIONS CONTAINING MONOPEROXY ACIDS

[75] Inventors: Christopher B. Guay; Joanna P. Hinton, both of Cincinnati, Ohio

[73] Assignee: The Procter & Gamble Company, Cincinnati, Ohio

[*] Notice: The portion of the term of this patent subsequent to Dec. 29, 2004 has been disclaimed.

[21] Appl. No.: 742,467

[22] Filed: Aug. 5, 1991

Related U.S. Application Data

[63] Continuation of Ser. No. 568,292, Aug. 16, 1990, abandoned, which is a continuation-in-part of Ser. No. 421,039, Oct. 13, 1989, abandoned.

[51] Int. Cl.$^5$ .......................... A61K 7/16; A61K 7/22
[52] U.S. Cl. .......................................... 424/53; 424/49
[58] Field of Search .................... 424/49, 53

[56] References Cited

U.S. PATENT DOCUMENTS

| | | | |
|---|---|---|---|
| 3,988,433 | 10/1976 | Benedict . | |
| 4,273,759 | 6/1981 | Gaffar | 424/54 |
| 4,490,269 | 12/1984 | Gallopo | 252/94 |
| 4,670,252 | 6/1987 | Sampathkumar | 424/53 |
| 4,716,035 | 12/1987 | Sampathkumar | 424/52 |
| 4,804,530 | 2/1989 | Sampathkumar | 424/53 |
| 4,886,658 | 12/1989 | Charbonneau et al. . | |
| 4,990,329 | 2/1991 | Sampathkumar | 424/53 |
| 4,994,262 | 2/1991 | Charbonneau et al. | 424/53 |
| 5,085,852 | 2/1992 | Banks | 424/49 |

FOREIGN PATENT DOCUMENTS 0066992 12/1982 European Pat. Off. .

OTHER PUBLICATIONS

Baldry, M. G. C., "The Antimicrobial Properties of Magnesium Monoperoxyphthalate Hexahydrate", Journal of Applied Bacteriology, 1984, 57, pp. 409-503.

Manly, Ind. Chemist 32:271-276 (1956) "Organic Peroxy Compounds in Industry".

*Primary Examiner*—Shep K. Rose
*Attorney, Agent, or Firm*—Douglas C. Mohl; Kim W. Zerby; Jack D. Schaeffer

[57] ABSTRACT

Disclosed are oral compositions useful for reducing plaque and gingival or periodontal diseases comprising monoperoxyphthalic acids and having a pH of from about 3.0 to about 5.0.

13 Claims, No Drawings

ORAL COMPOSITIONS CONTAINING MONOPEROXY ACIDS

This is a continuation of application Ser. No. 568,292 filed Aug. 16, 1990, which is a continuation-in-part application of application Ser. No. 421,039, filed Oct. 13, 1989, now both abandoned.

TECHNICAL FIELD

The present invention relates to compositions and methods for reducing dental plaque and gingival or periodontal diseases through the use of specific peroxy acid compositions.

BACKGROUND OF THE INVENTION

Peroxy compounds, including monoperoxyphthalic compounds, have been used in oral compositions for a variety of purposes such as stain reduction: U.S. Pat. Nos. 3,988,433 issued to Benedict on Oct. 26, 1976; 4,273,759 issued to Gaffar & Gaffar on Jun. 16, 1981; 4,490,269 issued to Gallopo on Dec. 25, 1984; and European Patent Application No. 0,133,354 of Interox Chemicals, Ltd., published Feb. 20, 1985. Monoperoxyphthalic acid compounds have also been disclosed in antigingivitis compositions: U.S. Pat. Nos. 4,670,252 issued to Sampathkumar on Jun. 2, 1987; and 4,716,035 issued Sampathkumar on Dec. 29, 1987.

The present inventors have discovered that by maintaining the pH of the monoperoxy compositions within a certain range enhanced effectiveness of the monoperoxy compounds is achieved.

It is an object of the present invention therefore to provide compositions and methods which provide for enhanced antiplaque and antigingivitis efficacy through the use of monoperoxy compositions.

It is a further object of the present invention to provide compositions which have enhanced efficacy but also have very low levels of stain.

These and other objects will become more apparent from the detailed description below.

All percentages and ratios herein are by weight unless otherwise specified. Also, all measurements are made at 25° C. unless otherwise specified.

SUMMARY OF THE INVENTION

The present invention relates to compositions and methods for treating or preventing plaque and gingival or periodontal diseases in humans and lower animals wherein such compositions comprise:
(a) a safe and effective amount of a monoperoxyphthalate compound;
(b) a suitable carrier;
wherein the composition has a pH of from about 3.0 to about 5.0.

A detailed description of the essential and optional components of the present invention are detailed below.

Monoperoxyphthalate Compounds

The present invention relates to monoperoxyphthalate compounds. As used herein, monoperoxyphthalate compounds have the structure:

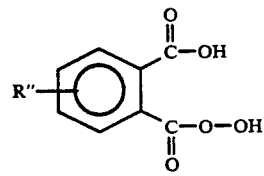

or the pharmaceutically acceptable salts or esters thereof, wherein R" may be one or more substituents compatible with the peroxy acid functionality of the aromatic ring.

By "substituents compatible with the peroxy acid functionality of the aromatic ring", as used, herein, is meant substituents on the ring which do not react with peroxy acids thereby reducing the stability and effectiveness of the compounds to treat diseases of the oral cavity. Nonlimiting examples of R" groups include hydrogen, hydroxy, substituted and unsubstituted saturated alkyl having from 1 to about 20 carbon atoms (e.g., methyl, ethyl), substituted and unsubstituted aryl (e.g., phenyl, naphthyl), substituted and unsubstituted benzyl, chloro, fluoro, nitro, sulphonate, trifluoromethyl, trialkylammonium (e.g., trimethylammonium, triethylammonium), cyano, carboxy, carboxylate (e.g., —COOCH$_3$), percarboxyl (e.g., —CO$_3$H), and alkoxy (e.g., methoxy, ethoxy). Preferred R" groups are hydrogen, saturated alkyl having from 1 to about 20 carbon atoms, aryl, benzyl, chloro, fluoro, carboxy, and alkoxy. Particularly preferred is R" being hydrogen. R" may also be an iodo, bromo, substituted or unsubstituted amino, or amido group, but such groups are generally not desirable since they can react with peroxy acid groups. Selection of substituents compatible with the peroxy acid functionality of the aromatic ring can easily be made by one skilled in the art.

By "pharmaceutically-acceptable salts or esters", as used herein, is meant esters and salts of substituted or unsubstituted monoperoxyphthalic acid compounds which have the same general antibacterial properties as the preferred magnesium salt of monoperoxyphthalic acid, and which are acceptable from a toxicity viewpoint. Nonlimiting examples of pharmaceutically-acceptable salts include alkali metal (e.g., sodium, potassium), alkaline earth metal (e.g., calcium, magnesium), non-toxic heavy metal, and tetraalkylammonium (e.g., tetraethylammonium). Preferred compounds useful in the present invention are the substituted or unsubstituted monoperoxyphthalate compounds with pharmaceutically-acceptable divalent cation salts (e.g., magnesium, calcium), and the magnesium salt being the most preferred.

Most preferred for use in the present invention is the magnesium salt of monoperoxyphthalic acid. This magnesium salt is the salt of the carboxylic acid group only, having the structure:

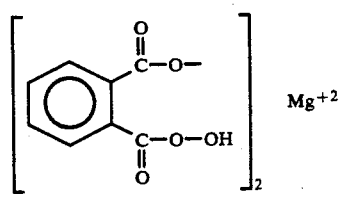

(hereinafter referred to as "PAM"), as disclosed in European Patent Application No. 27,693, published Apr. 29, 1981, filed by Interox Chemicals, Ltd., the disclosure of which is incorporated herein by reference. The compound is a hydrate when in its solid form. Synthesis of the compound is also disclosed. This compound is also commercially available from Interox Chemicals Limited.

Synthesis of substituted and unsubstituted monoperoxyphthalate compounds can be achieved by those skilled in the art using methods disclosed in, for example, in addition to European Patent Application No. 27,693, European Patent Application No. 66,992 to Interox Chemicals Ltd.; U.S. Pat. No. 3,075,921 to Brockelhurst, et al.; "Organic Peroxides", Daniel Swern, Editor, published 1970 by John Wiley & Sons, Inc.; and in British Patent Specification No. 1,378,671; the disclosures of all of which being incorporated herein by reference.

Suitable Carriers

Since the monoperoxy phthalate compounds are unstable in aqueous or polar solvent media or to exposure to oxidizing/reducing agents, care must be taken to avoid exposure of the compounds to such materials where it is desired to have the materials in the compositions in total. One way to accomplish this is to have two compositions which are combined just prior to insertion of the mixed composition into the mouth. Due to aesthetic reasons, the anhydrous monoperoxy phthalate part of a toothpaste composition would be less than the amount of a major phase which would be more like a conventional toothpaste. Of course single phase anhydrous systems or systems wherein the peroxy compound in powder form may be added to a composition containing potentially unstabilizing components immediately prior to use.

Whatever form the compositions take the monoperoxy phthalate concentration in the final (mixed) formulation should be in the range of 0.01% to about 10%, preferably in the range of 0.1% to about 7.5%, more preferably in the range of 0.25% to about 5%.

Also the final formulation put into the mouth should have a pH of from about 3 to about 5, preferably from about 3.5 to about 5, more preferably from about 4.0 to about 4.7 and be safe to tooth enamel. The pH control agents can be any agents which buffer in the desired pH range. Such agents include organic agents such as mono-, di-, tri as well as higher polycarboxylates and amino carboxylates. Included among such agents are citric acid, malic acid, tartaric acid and gluconic acid among many others.

Inorganic agents may also be used and include phosphates and polyphosphates such as pyrophosphate. Phosphonates such as ethylene hydroxy diphosphonate may also be used.

Looking now at materials which may comprise the remainder of the peroxy acid minor portion of a toothpaste composition, for example, they include:

Solvent

Solvents that are compatible with the peroxy acid can be used. The preferred levels of the solvent are 1–95% of the minor, more preferred in the range of 5–90% and the most preferred range of 10–70%. In general terms, compatible solvents do not appreciably solubilize the proxy acid. In practice, solvents include (1) natural hydrocarbons of the general form ($C_nH_{2n+2}$), wherein $n=1$, (2) triacetin and other fully esterified glycerols, (3) vegetable oils, (4) some high molecular weight polyethylene glycols (likely also are polyacids such as polyphosphate, polysulfonic; these acids are unlikely to react since they are already highly oxidized).

Thickening Agent

Thickening agents in the range of 1–95% of the minor phase formulation, more preferably in the range of 5–90% and most preferred in the range of 10–70%. These thickening agents must be substantially compatible with the peroxy acid and can thicken nonaqueous nonpolar systems. Thickening agents that are useful include (1) natural hydrocarbons (paraffin waxes, petroleum jellies), (2) high molecular weight synthetic alkanes (allied Signal-homopolymers Ac-x), (3) inert building/thickening agents including silicas (precipitated, fumed and silica gels), clays (Bentone gels, Veegums), diatomaceous earth, and synthetic silicates (Zeolites).

Other Components

Components of Major Phase

The major, nonperoxy acid composition can contain any of the conventional components present in aqueous toothpaste compositions. Optional components include: aesthetic additives can be added such as oxidation stable colors, flavors, and sweeteners in the range of 0.1% to 20% of the major phase formulation.

Dentifrices generally contain an abrasive polishing material and typically also contain sudsing agents, flavoring agents and sweetening agents. Toothpaste compositions additionally contain binders, humectants and water.

The dentifrice abrasive, generally has a particle size of from about 0.1 to about 10 microns in diameter and can be any abrasive polishing materials which does not excessively abrade tooth dentin. These include, for example, silica, both precipitated and gels, calcium carbonate, dicalcium orthophosphate dihydrate, calcium pyrophosphate, calcium polymethaphosphate and insoluble sodium polymetaphosphate. Preferably, however, the abrasive is one which has a high degree of compatibility at low pH's with the peroxy compounds and fluoride ions. These include, for example silica xerogels such as those described in U.S. Pat. No. 3,538,230 to Pader et al., issued Nov. 3, 1970; hydrofluoric acid-treated amorphous silica abrasives such as those disclosed in U.S. pat. No. 3,862,307 to DiGiulio, issued Jan. 21, 1975; mineral abrasives coated with cationic polymers such as those disclosed by J. J. Benedict in U.S. Pat. No. 4,157,387, issued Jun. 5, 1979; and condensation products of urea and formaldehyde such as those disclosed in Cooley et al., in U.S. Pat. No. 3,070,510, issued Dec. 24, 1972. All of these patents are incorporated herein by reference.

The total amount of abrasive materials in the dentifrice embodiments of this invention can range from about 0.5% to about 95% by weight of the dentifrice. Preferably toothpastes contain from about 6% to about 60% by weight and toothpowders contain from about 20% to about 95% by weight abrasives.

Dentifrice compositions can also contain emulsifying agents. Suitable emulsifying agents are those which are reasonably stable and foam throughout a wide pH range, including nonsoap nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide anticaries effectiveness. The fluoride compounds are believed to provide protection against demineralization as well as aid in remineralization of dental enamel. Preferred fluorides are sodium fluoride, stannous fluoride, indium fluoride, and sodium monofluorophosphate. Norris et al., U.S. Pat. No. 2,946,725, issued Jul. 26, 1960 and Widder et al., U.S. Pat. No. 3,678,154, issued Jul. 18, 1972 disclose such salts as well as others.

In preparing toothpastes, it is necessary to add some thickening material to provide a desirable consistency. Preferred thickening agents re carboxyvinyl polymers, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols.

The humectant can comprise up to about 65% by weight of the toothpaste composition.

With both humectants and binders, care must be taken if these are combined with the peroxy compound that they do not activate the compound before the product is used.

Flavoring agents can also be added to dentifrice compositions. Suitable flavoring agents include oil of wintergreen, oil of peppermint, menthol, oil of spearmint, oil of sassafras, and oil of clove. Sweetening agents which can be used include aspartame, magna sweet, acesulfame, saccharin, dextrose, levulose and sodium cyclamate. Flavoring and sweetening agents are generally used in dentifrices at levels of from about 0.005% to about 2% by weight.

Another preferred embodiment of the major portion present invention is a mouthwash composition. Mouthwashes generally comprise about 20:1 to about 2:1 of a water/ethyl alcohol solution and preferably other ingredients such as fluoride ion sources, flavor, sweeteners, humectants, and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06) sweetening agent such as saccharin, 0% to about 1.67% fluoride ions (preferably from about 0.0017% to about 0.67%), 0% to 0.3% (preferably 0.03% to 0.3%) flavoring agent, and the balance water.

The minor portion if in mouthwash form would contain only anhydrous materials such as glycerin or similar materials.

The compositions of the present invention may also include tartar control agents and antidemineralization agents.

Tartar control agents can be added to this formulation to provide additional consumer benefits. Agents which can chelate calcium or prevent the crystallization/crystal growth of calcium phosphates are useful. Included in this group are chelating agents (EDTA, NTA, other carboxylates, aminocarboxylates), and agents which prevent crystal growth of natural calcium phosphates in the mouth. Such agents include (1) polyphosphates (including pyrophosphate and phosphocitrate, at least at 0.5%, preferably in the range of 1–10% and most preferably in the range of 2–6%), (2) phosphonates (including linear and cyclic alkyl diphosphonates at least at levels of 0.25%, more preferably in the range of 0.5–10% and the most preferred range of 1–6%), and (3) zinc containing components in the range of 0.1% to 10%, more preferably in the range of 0.25% to 7.5% and most preferred in the range of 0.5–5% on a zinc basis. The zinc should be complexed to allow for efficacious soluble levels of zinc. Chelators are effective complexing agents and carboxyl based chelating agents are preferred, especially citrate.

Materials that can prevent/slow down the demineralization of enamel and dentin are useful in this range of pH's below 4. Included are fluorides, phosphates, pyrophosphates, stannous ion, indium ion, titanium ion, zinc ion. Levels that effectively protect the enamel surface range from 0.01% to 10%.

In addition to toothpaste and mouthwash compositions, the peroxy acid component can be formulated as a dry powder or tablet or capsule with dry flavoring, sweetening agents and mixed with an aqueous solution just prior to use in the mouth.

METHOD OF MANUFACTURE

Minor Phase

A method for manufacturing the minor phase of Example VI is as follows: the mineral oil is heated to approximately 55° C. with agitation. The petrolatum is then added, again with agitation. The combination is mixed vigorously for about two minutes. The heat source is removed and the peroxy acid is slowly dispersed in the mixture. The mixing of these materials is such to produce a smooth and creamy texture. The material is then milled, deaerated and packed into appropriate packages.

In addition to the oil/wax formulations described above, silica (such as the high oil absorbency silicas, Zeodent 163, Zeothix 265 manufactured by Humber Chemical Co.) can replace the wax. Other high oil absorbency silicas (fumed, precipitated and silica gels) can also replace the wax.

Typically the manufacturing of this phase is accomplished by adding the oil (all acceptable grade mineral oils as differentiated by viscosity) to an appropriate mixing system, such as a double planetary mixer or other appropriate bath processing system, and then adding the silica. This is mixed at ambient temperature to achieve a stable gel. The active ingredient, PAM, is then added to the system at ambient temperature. Other acceptable excipients, sweeteners (such as monoammonium glycerrhyzinate, saccharin, cyclamates) or inert, unreactive components are added at this time. The system is mixed to achieve a homogeneous suspension.

The physical stability of these systems depends on the PAM concentration and the silica/oil (w/w) ratio. For high total solids levels (40–60% (w/w) determined as the sum of the PAM and the excipients, but not including the silica), a silica/oil ratio of 0 to 0.2 is preferred. At lower solids levels (less than 40%), higher silica/oil ratios are needed to achieve homogeneous, physically stable formulations. These formulations are designed to attain a balance between physical stability and acceptable rheology.

These systems (mineral oil/wax/PAM and mineral oil/silica/PAM) described above are amenable to continuous processing as well as batch processing.

Major Phase

The manufacturing of the major phase parallels typical dentifrice manufacturing. The water is added to an appropriate mix tank and heated. An adequate amount of humectant is added to the mix tank and agitated for 2-5 minutes. The basic form of the buffer is added and dissolved in the mix tank. The components are agitated in the tank to ensure complete dissolution of this material. The acidic form of the buffer is then added followed by the sweetener. All components are agitated to ensure complete dissolution and mixing. The abrasive is slowly added to the mix tank with agitation. This is agitated for approximately 10 minutes, increasing speed of mixer as appropriate. The fluoride is added to the mix tank as is the opaquing agent (if any). The foaming agent is then added and mixed slowly to fully disperse the components. In a separate mix tank, the remaining humectant is added and the binder(s) are dispersed into the humectant. This mixture is agitated to an appropriate consistency. The binder slurry is added to the main mix tank and agitated. Any color and flavor components are added and the mixture is agitated to an appropriate consistency. The mixture is milled, dearated and packed into appropriate packages.

A process for manufacturing powders of the type disclosed in Examples XII-XV can be as follows. The peroxy acid, the buffers and the sweetener are mixed in a blender and mixed for two minutes. The flavor and dyes, if present, are then added and the entire mixture is mixed for ten minutes.

COMPOSITION USE

The compositions of the present invention are used by combining the two phases, if present, just prior to use and used by the user for a period of normal use (e.g., 10 seconds to 5 minutes).

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES I-X

Given below are toothpaste compositions representative of the present invention:

| Component | Weight % | | | | |
|---|---|---|---|---|---|
| Major Phase | I | II | III | IV | V |
| Sodium Fluoride | 0.270 | 0.270 | 0.270 | 0.270 | 0.270 |
| Sodium Citrate | 4.390 | 10.000 | 4.500 | 6.500 | |
| Citric Acid | 1.000 | 5.000 | 0.820 | | |
| Sodium Dihydrogen Phosphate | | 2.000 | | 3.000 | |
| Tetrasodium Pyrophosphate | | | | | 3.400 |
| Sodium Acid Pyrophosphate | | | | | 1.370 |

-continued

| | | | | | |
|---|---|---|---|---|---|
| Saccharin | 0.300 | 0.150 | 0.300 | 0.300 | 0.280 |
| Sorbitol | 40.370 | 34.160 | 27.620 | 30.000 | 30.000 |
| Silica | 20.000 | 22.000 | 20.000 | 24.000 | 22.000 |
| Carbopol | | | 0.350 | 0.250 | 0.350 |
| Xanthan Gum | | | 0.700 | 0.800 | |
| Carrageenan | | | | | 0.550 |
| Carboxy methyl Cellulose (CMC) | 1.100 | 1.300 | | | |
| Glycerin | 10.000 | | | | |
| Sodium Alkyl Sulphate | 4.00 | 4.000 | 5.000 | 4.000 | 4.000 |
| PEG-12 | | | 1.000 | 2.000 | 1.000 |
| Titanium Dioxide | 0.525 | 0.525 | 0.525 | | 0.525 |
| Color | 0.050 | 0.100 | 0.100 | 0.100 | 0.050 |
| Flavor | 1.100 | 1.100 | 1.100 | 1.000 | 1.044 |
| Adjust pH to | 5.0 | 4.5 | 5.5 | 5.0 | 6.5 |
| Water q.s. to | 100% | 100% | 100% | 100% | 100% |
| Minor Phase | VI | VII | VIII | IX | X |
| (87.4% MMPP)* | 57.470 | 57.400 | 35.000 | 57.400 | 57.400 |
| Mineral Oil | 25.520 | 23.900 | 34.273 | 10.000 | |
| Petrolatum | 17.010 | 15.700 | 29.272 | | 33.545 |
| Petroleum Jelly | | | | 31.600 | |
| Sodium Saccharin | | | 0.455 | | 0.455 |
| Silica | | 3.000 | 1.000 | | |
| Cab-O-Sil | | | | 1.000 | |
| AC-6 | | | | | 7.500 |
| Flavor | | | | | 1.100 |
| | 100.000 | 100.000 | 100.000 | 100.000 | 100.000 |

*MMPP = Magnesium salt of monoperoxyphthalic acid

EXAMPLE XI

Given below is another toothpaste composition of the present invention:

| Component | Level (%) | Level Delivered at 90:10 Ratio of Major Phase:Minor Phase |
|---|---|---|
| Major Phase (90% of Delivered Product) | | |
| Water | 28.74 | 25.866 |
| Sodium Saccharin | 0.30 | 0.270 |
| Sodium Fluoride | 0.27 | 0.243 |
| Sodium Citrate | 4.50 | 4.050 |
| Citric Acid (Anhydrous) | 0.82 | 0.738 |
| Sorbitol | 27.62 | 24.858 |
| Titanium Dioxide | 0.50 | 0.450 |
| Silica | 20.00 | 18.000 |
| Sodium Alkyl Sulfate (27.9% Soln) | 5.00 | 4.500 |
| Glycerin | 10.00 | 9.000 |
| Xanthan Gum | 0.70 | 0.630 |
| Carbopol | 0.35 | 0.315 |
| Flavor | 1.10 | 0.990 |
| Color | 0.10 | 0.090 |
| Total | 100.00 | 90.000 |
| Minor Phase (10% of Delivered Product) | | |
| Mineral Oil | 25.70 | 2.570 |
| Petrolatum | 17.10 | 1.710 |
| PAM (87.4% MMPP) | 57.20 | 5.720* |
| Total | 100.00 | 10.000 |

*(5.0% MMPP)

EXAMPLES XII-XV

Given below are examples of powders according to the present invention:

| | XII | XIII | XIV | XV |
|---|---|---|---|---|
| MMPP | 12.666 | 22.275 | 37.480 | 12.666 |
| Sodium Carbonate | 5.431 | 4.760 | 4.013 | 5.431 |
| Sodium Bicarbonate | 29.872 | 27.368 | 22.070 | 29.872 |
| Sodium Saccharin | 2.716 | 2.380 | 2.006 | 2.716 |
| Menthol | 4.073 | 3.570 | 3.010 | 4.073 |
| Sodium Lauryl Sulfate | 1.792 | 1.570 | 1.324 | 1.792 |

-continued

| | XII | XIII | XIV | XV |
|---|---|---|---|---|
| Citric Acid | | 38.077 | 30.097 | |
| Malic Acid | | | | 43.450 |
| Sodium Phosphate | 20.000 | | | |
| Tartaric Acid | 23.450 | | | |
| Total | 100.000 | 100.000 | 100.000 | 100.000 |
| Grams of formulation added to 15 mls water | 0.368 | 0.420 | 0.498 | 0.368 |

What is claimed is:

1. A composition for treating or preventing dental plaque, or gingival or periodontal diseases of the oral cavity in humans or lower animals comprising:
   (a) a safe and effective amount of a monoperoxyphthalate compound having the structure:

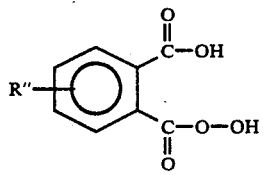

or the pharmaceutically acceptable salts or esters thereof, wherein R" is one or more substituents compatible with the peroxy acid functionality of the aromatic ring; and
   (b) a suitable carrier;
wherein said composition has a pH of about 3.0 to about 5.0 and contains a mono-, di- or tricarboxylic acid buffering agent.

2. The composition of claim 1 wherein R" is selected from the group consisting of hydrogen, substituted and unsubstituted saturated alkyl having from 1 to about 20 carbon atoms, substituted and unsubstituted aryl, substituted and unsubstituted benzyl, chloro, fluoro, nitro, sulfonate, trifluoromethyl, trialkylammonium, cyano, carboxy, carboxylate, percarboxy, hydroxy, and alkoxy.

3. The composition of claim 2 wherein R" is selected from the group consisting of hydrogen, saturated alkyl having from 1 to about 20 carbon atoms, phenyl, benzyl, chloro, fluoro, carboxy, and alkoxy.

4. The composition of claim 3 wherein R" is hydrogen.

5. The composition of claim 1 wherein the monoperoxyphthalate compound has the structure:

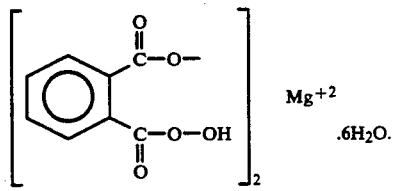

6. The composition of claim 1 which comprises two separate compositions, one containing monoperoxy phthalate compound and the other containing the acid buffering agent.

7. The composition of claim 6 wherein the composition is a toothpaste and wherein the monoperoxy phthalate composition is anhydrous and the acid buffering composition is an aqueous composition.

8. The composition of claim 7 wherein the acid buffering component is citric acid.

9. The composition of claim 8 wherein the monoperoxy phthalate composition contains mineral oil and petrolatum or a silica abrasive.

10. A method of reducing plaque and gingivitis comprising contacting the gums and teeth of a human or lower animal with the composition of claim 1.

11. A method according to claim 10 wherein the composition is a toothpaste.

12. A method according to claim 11 wherein the acid buffering agent is citric acid.

13. A method according to claim 10 wherein the composition is a mouthrinse.

* * * * *